United States Patent [19]

Bernsen

[11] 4,007,326

[45] Feb. 8, 1977

[54] ELECTRONIC COPY ANALYSIS

[75] Inventor: Borg Bernsen, Buena Park, Calif.

[73] Assignee: Xerox Corporation, Stamford, Conn.

[22] Filed: Jan. 15, 1976

[21] Appl. No.: 649,301

[52] U.S. Cl. .......................... 358/280; 178/DIG. 1; 178/DIG. 37; 356/165; 356/167; 358/106

[51] Int. Cl.² ...................... G01B 9/08; H04N 7/18

[58] Field of Search ................. 178/6.8, 6, DIG. 1, 178/DIG. 6, DIG. 35, DIG. 36, 7.6; 350/158, 160, 165, 166, 167

[56] References Cited

UNITED STATES PATENTS 3,283,071 11/1966 Rose .............................. 178/DIG. 1
3,560,093 2/1971 Montone .......................... 356/165
3,740,467 6/1973 Kubo ............................. 178/6.8

Primary Examiner—Benedict V. Safourek
Assistant Examiner—Edward L. Coles

[57] ABSTRACT

An apparatus for analyzing and comparing the copy quality of the copies of an original to the original. The apparatus includes a 50% transmission/50% reflection mirror, a vidicon for scanning the original and its copy through the mirror, means for reading out the vidicon images of the original and the copy, and means for comaring and analyzing the copy and the original for generating a comparison signal.

5 Claims, 2 Drawing Figures

ELECTRONIC COPY ANALYSIS

This invention relates to an apparatus for determining copy quality and, more particularly, an apparatus for comparing a copy to its original and thus measure the copy quality of a copier/duplicator.

BACKGROUND OF THE INVENTION

According to the prior art such as that shown in the U.S. Pat. No. 3,546,377 issued to John Troll on June 12, 1968, an apparatus having two vidicons with delayed scanning means may be used to scan a sample and a standard profile, respectively. As disclosed, the two vidicon outputs are synchronized in time and compared through a differential comparator. A comparator signal output which is above a predetermined threshold is employed to indicate the lack of coincidence and rejection of the sample.

SUMMARY OF THE INVENTION

It is a general object of the present invention to provide an improved video means comparing for a copy to its original and a specific object of the present invention to provide simplified and improved means for comparing and analyzing the quality of a copy to its original.

The objects of the present invention are achieved by utilizing a vidicon and a partially reflecting - partially transmitting mirror positioned so as to permit the simultaneous viewing of the original document and the reproduced document. Apparatus is provided for comparing the difference in the signals between the superimposed document and for analyzing the difference to provide a signal related to the copy quality.

These and other features of the invention will be understood upon reading the following description along with the drawings.

FIG. 1 is a schematic drawing of the apparatus according to the present invention, and FIG. 2 illustrates several wave forms useful in explaining the operation of the apparatus shown in FIG. 1.

DETAILED DESCRIPTION OF THE INVENTION

According to the present invention, the copy comparison and analysis apparatus is based upon a measured and identified difference of degradation between a standard test pattern and a copy of this pattern.

Figure 1:
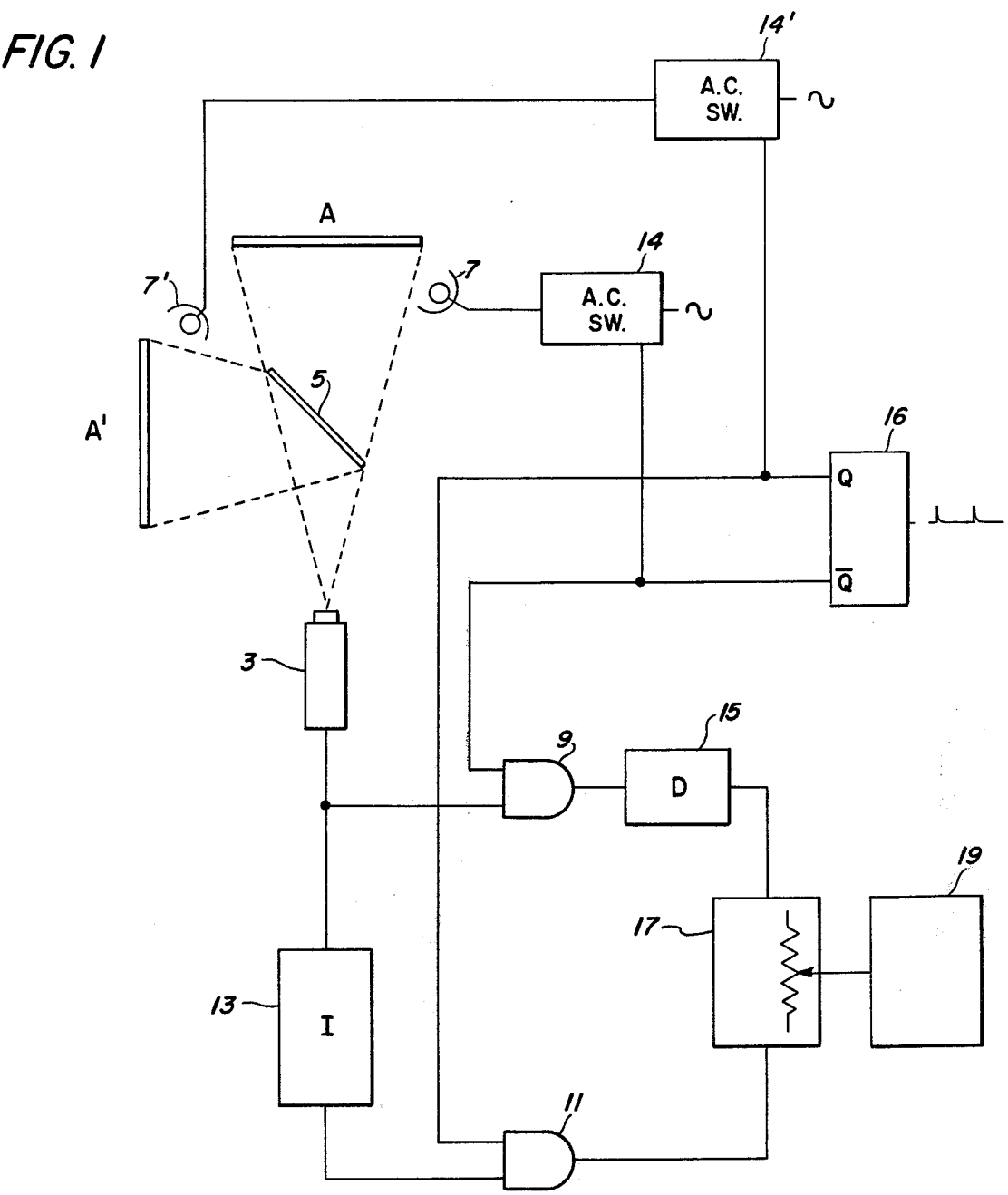

Referring to FIG. 1, a standard test pattern A is viewed by a television camera or vidicon 3 at a suitable resolution. A 50% transmission/50% reflection mirror 5 is so positioned that a copy A' of the standard pattern A is exactly superimposed on the image of the standard pattern A.

The standard test pattern A and the copy A' are illuminated by two light sources 7 and 7' in succession so that a complete TV picture frame is obtained first from the pattern A and then the copy A'. The video signal at the output of the TV camera 3 is sampled by suitable gates 9 and 11 in succession so that the video output of the vidicon 3 for the standard pattern A is gated through the gate 9 when the standard pattern A is illuminated and the video output of the vidicon 3 for the copy A' is phase inverted by a phase inverter 13 and gated through the gate 11 when the copy A' is illuminated. While the gates 9 and 11 are shown symbolically as coincidence gates, other suitable means such as field effect transistor amplifiers configured to function as coincidence gates could be used.

Figure 2:
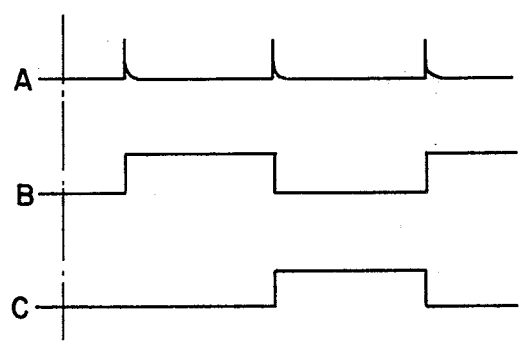

The operation of the gates 9 and 11 and the lights 7 and 7' may be synchronized as follows. Two AC switches 14 and 14' and the two gates 9 and 11 are actuated by two enabling signals (FIG. 2, curves B and C) produced in succession by a suitable means such as a flip flop 16. The flip flop 16 may be triggered in a well known manner by a train of pulses (FIG. 2, curve A) having a suitable repetition rate timed to coincide with the rate at which it is desired for the video camera 3 to obtain picture frames of the pattern A and then the copy A'. For the AC switches 14 and 14', a suitable arrangement such as a photodiode switch may be used although any other suitable AC switches could be used.

The output of the gate 9 is connected to a delay means 15 which introduces a necessary delay so that the video image signals from both the standard pattern A and the copy A' coming through via the gates 9 and 11 respectively appear simultaneously at a comparator 17. The comparator 17 may be of any suitable design such as a balance potentiometer. The output of the comparator 17 is then applied to a video monitor 19 of conventional design which is biased to the center of a gray scale. As evident from the foregoing, the output of the comparator 17 appearing at the input to the monitor consists of the composite of the "white" modulated image from the standard pattern A and "black" modulated image from the copy A'. By accurately aligning the copy and the standard and by controlling the image contrast, the two modulated images are allowed to cancel each other out if no difference exists. However, if a degradation has taken place during the copy process so that there exists defects in the copy, then the defects will be displayed in the form of a different signal on the monitor. By analyzing the difference using suitable technique such as computer analysis technique based on communication and information theories, quantified measures of the differences can be obtained, permitting identification of the defects in or quality of the copy.

While the copy comparison and analysis means of the present invention is illustrated with a specific embodiment, various modifications and changes may be made thereto by those skilled in the art without departing from the spirit and scope thereof.

What is claimed is:

1. An apparatus for comparing the quality of a copy of a standard pattern to its original, comprising:
    a vidicon:
    a substantially half and half transmission/reflection mirror so interposed between said vidicon and the copy and the original that the image of the copy is superimposed on the image of the original formed on said vidicon;
    means for illuminating the original and the copy in sucession in such a manner that said vidicon forms a video image of the original and a video image of the copy; and,
    means for comparing the copy image to the original image and generating a comparison signal;
    said means for comparing and generating a comparison signal includes;
    a comparator;
    delay means;
    first gating means for gating the output of said vidicon to said comparator via said delay means;

inverting means for inverting the output of said vidicon;

second gating means for gating the output of said inverting means to said comparator;

means for actuating said first and second gating means in sucession in synchronization with the illumination of the original and the copy; and, whereby said comparator receives the video images of the original and the copy simultaneously and generating the comparison signal indicative of the difference between the original and the copy.

2. The apparatus according to claim 1, including computer means for analyzing the comparison signal for rating the copy quality.

3. The apparatus according to claim 1, wherein said comparing means includes a potentiometer which is so balanced that the output thereof registers zero reading when the video image from the output of said inverting means is in inverse of the video image of the original thereby signifying that the copy is a good quality.

4. The apparatus according to claim 3, including a video monitor biased to the center of gray scale so that said monitor registers zero difference between the original and copy and registers a difference signal the level of which is proportionate to the degree of degradation of the copy over the original.

5. The apparatus according to claim 3, wherein the copy and the original are aligned and the video image contrasts are so controlled that in said comparing means the 'white' modulated video image from said vidicon via said first gating means cancels out the 'black' modulated image output from said inverting means when said copy is of a good quality and wherein said apparatus further includes computer analysis means for analyzing the difference signal produced by said comparing means indicative of the defect in the quality of the copy; and, providing quantified measure of indication of the defect from said difference signal.

* * * * *